United States Patent [19]

Williams

[11] 4,169,550

[45] Oct. 2, 1979

[54] EMERGENCY MEDICAL KIT

[75] Inventor: Paul K. Williams, Arlington, Tex.

[73] Assignee: Emergency Medical Equipment Incorporated, Oklahoma City, Okla.

[21] Appl. No.: 796,410

[22] Filed: May 12, 1977

[51] Int. Cl.² .............................................. A45F 3/00
[52] U.S. Cl. .................................. 224/211; 206/803; 190/41 Z; 190/52
[58] Field of Search .............. 206/570, 803; 190/41 Z, 190/43, 49, 51, 52; 224/8 R, 5 BC, 6

[56] References Cited

U.S. PATENT DOCUMENTS

| | | | |
|---|---|---|---|
| 1,387,597 | 8/1921 | Fetters | 190/43 |
| 3,110,376 | 11/1963 | Naab et al. | 190/41 Z |
| 3,315,772 | 4/1967 | Katz | 190/43 |
| 3,780,857 | 12/1973 | Rosano, Jr. et al. | 206/803 |
| 3,799,414 | 3/1974 | Fiffer | 224/6 |
| 3,885,722 | 5/1975 | Robertson | 224/5 BC X |
| 3,951,260 | 4/1976 | Frazze | 206/803 |
| 3,994,372 | 11/1976 | Geller et al. | 190/43 |

Primary Examiner—Joseph Man-Fu Moy
Attorney, Agent, or Firm—Dunlap, Codding & McCarthy

[57] ABSTRACT

An emergency medical kit having a plurality of pockets and straps which are designed to hold medical equipment, the pockets being selectively closable to prevent the loss of the equipment retained therein. In an unfolded position, the medical kit can be spread upon a flat surface, or suspended from a hanger, such that the medical equipment is readily accessible to medical personnel. In a folded position, the medical kit is attachable to a person's back so that the medical equipment and supplies can be transported to areas inaccessible via motor vehicles.

2 Claims, 8 Drawing Figures

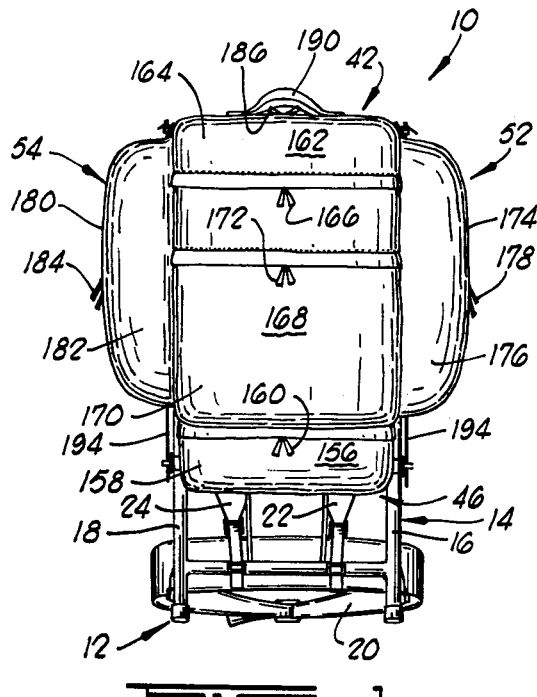
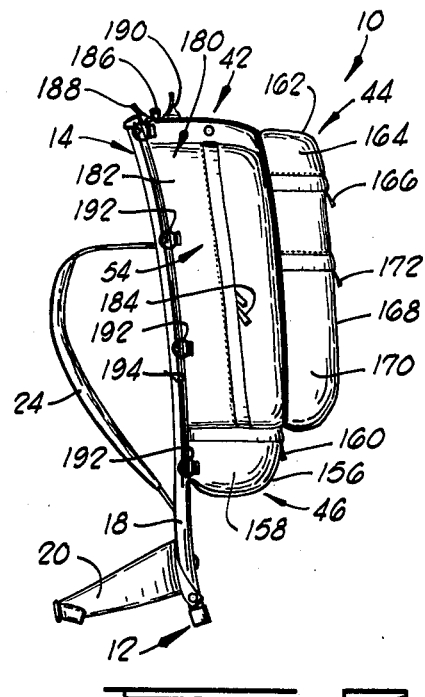
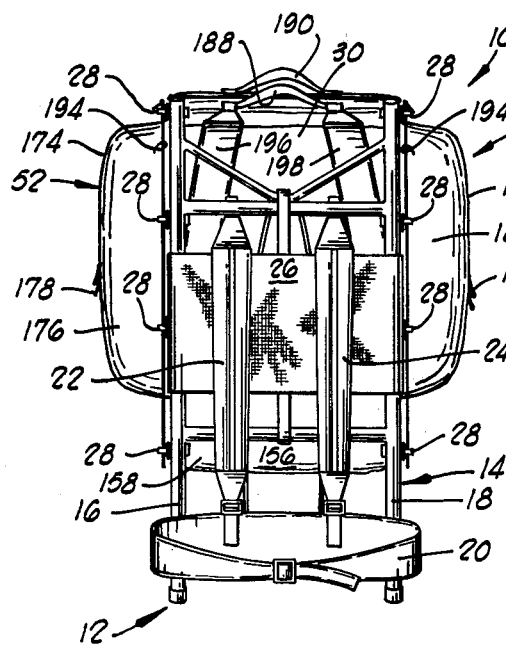
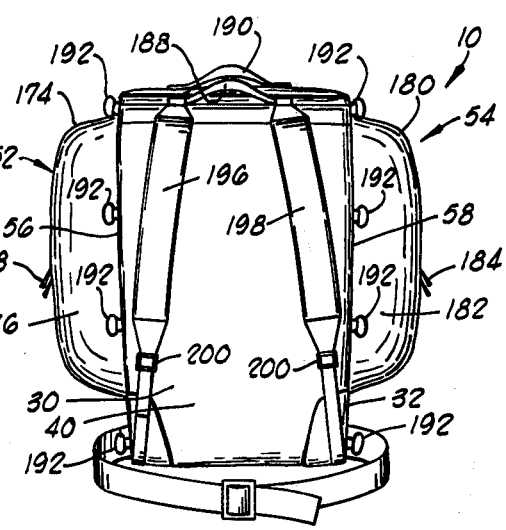

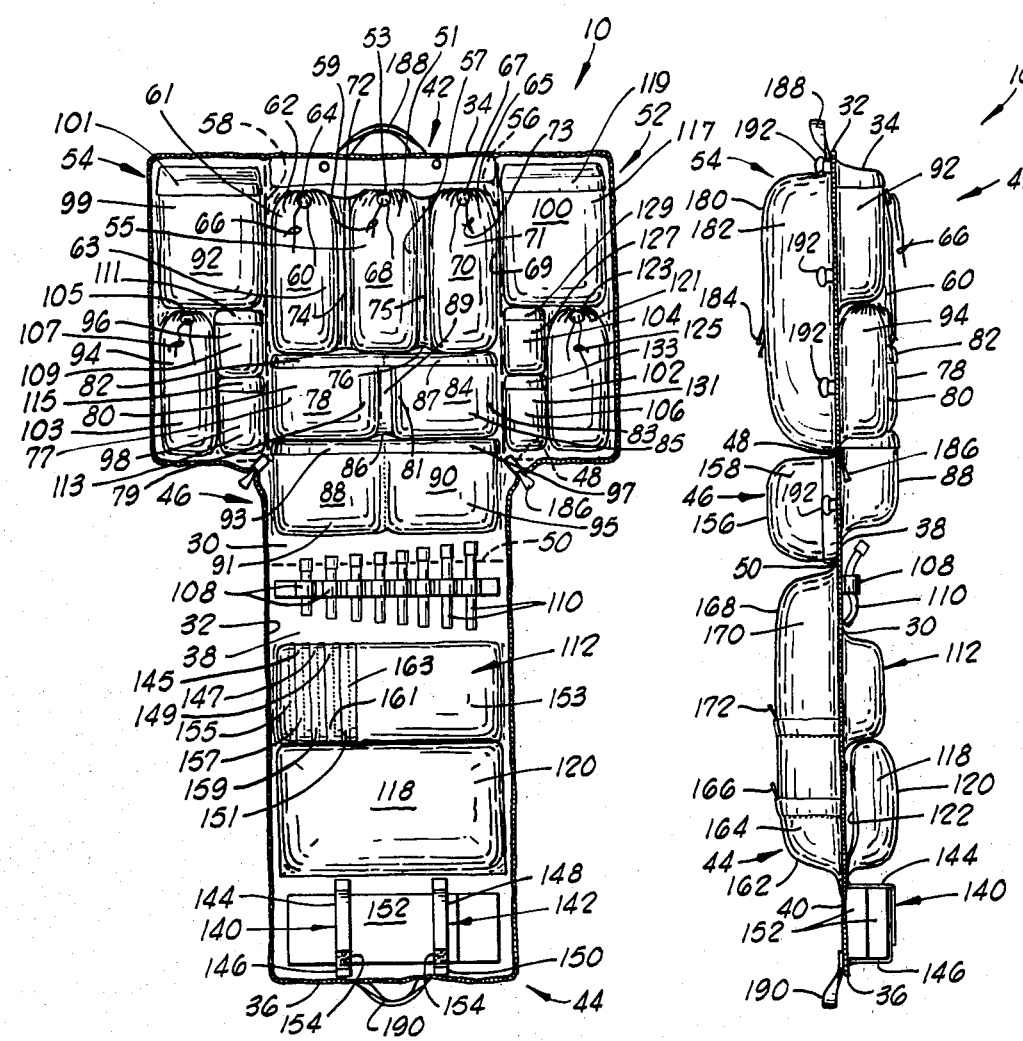

4,169,550

EMERGENCY MEDICAL KIT

BACKGROUND OF THE INVENTION

1. Field of the Invention

The present invention relates generally to portable storage apparatus, and, more particularly, but not by way of limitation, to emergency medical apparatus.

2. Prior Art

The efficency at which medical aid is rendered to an accident victim can, without a doubt, affect the resulting condition of the injured person. Sometimes minutes, or even seconds, may determine whether an accident will cause temporary or permanent injury to its victim. The matter of life or death may even depend upon the ability, or the inability, of medical personnel to treat a serious injury immediately, and in a professionnal manner.

An injured person is generally taken to a clinic or a hospital emergency room when a serious accident occurs. If this is not possible, a group of medical personnel is usually dispatched to the accident location via a motor vehicle equipped with medical supplies. However, in some instances, the injured person may be remotely located from an emergency room in an area that is inaccessible via a motor vehicle. If this is the case, the medical personnel may have to travel on foot to reach the accident victim. Since the injured person may require immediate attention, it would be desirable to carry at least some general purpose medical supplies, such as bandages and pain reducers, to the accident location. As a result, the victim could, at least, be rendered first aid until moved to a proper treatment facility.

One major problem may arise by taking only first aid equipment to the accident location. If the injured person is in a critical condition, first aid supplies may provide little, if any, effective treatment. Therefore, it would be more than desirable to have a complete assortment of emergency medical supplies and equipment, assembled in a portable fashion, in the form of an "emergency medical kit", for example. A medical doctor, a paramedic, or any comparably trained person, would thereby be enabled to perform emergency surgery or life-saving treatment upon an accident victim at virtually any geographical location.

The familiar back pack, commonly used for hiking and camping, does indeed provide a portable apparatus which would serve fairly well for the transport of most any type of articles, medical equipment and supplies included. An example of such a back pack is disclosed in the U.S. Pat. No. 2,764,327, issued to R. T. Stevenson. However, most commercially available back packs are constructed to hold camping equipment, or the like, and not medical equipment. Many articles utilized in the treatment of accident victims are in the form of small precision instruments, or are retained in breakable containers. Some loss of, and damage to, the medical equipment and supplies would likely result if a conventional back pack was utilized as an "emergency medical kit".

BRIEF DESCRIPTION OF THE DRAWINGS

FIG. 1 is a front elevational view of an emergency medical kit constructed in accordance with the present invention, the emergency medical kit being shown in a folded position and in combination with a pack support frame.

FIG. 2 is a side elevational view of the emergency medical kit shown in FIG. 1.

FIG. 3 is a rear elevational view of the emergency medical kit shown in FIG. 1.

FIG. 4 is a rear elevational view of the emergency medical kit, as shown in FIG. 3, with the pack support frame removed.

FIG. 5 is an elevational view of the emergency medical kit shown in FIGS. 1 through 4, the emergency medical kit being shown in an unfolded position in FIG. 5.

FIG. 6 is a side elevational view of the emergency medical kit shown in FIG. 5.

FIG. 7 is a view of a portion of the emergency medical kit shown in FIG. 5, this portion being shown in an unfolded position.

FIG. 8 is a side elevational view of the portion of the emergency medical kit shown in FIG. 7.

DESCRIPTION OF THE PREFERRED EMBODIMENT

Referring to the drawings in general, and to the FIGS. 1 through 3 in particular, shown therein and designated by the general reference numeral 10 is an emergency medical kit constructed in accordance with the present invention. The emergency medical kit 10 (sometimes herein simply referred to as the kit 10) is particularly useful for transporting emergency medical equipment to emergency accident locations which are remote from a hospital or an emergency medical facility. The kit 10 is preferably transported to remote locations via being carried upon a person's back. As shown in FIGS. 1, 2 and 3, the kit 10 is constructed to be utilized with a conventional pack support frame 12.

The kit 10 has a folded, or closed position, as shown in FIGS. 1 through 4, and an unfolded, or open, position, as shown in FIGS. 5 through 8. The kit 10 is preferably maintained in the folded position when being transported. During use, the kit 10 may be positioned in the unfolded position in a manner to be made more apparent below.

The emergency medical kit 10 also is useful in a variety of situations where it is desirable to have medical equipment displayed or stored in a readily accessible manner for convenient use via medical personnel. For example, the kit 10 may be manipulated to the unfolded position, as shown more clearly in FIGS. 5 and 6, and suspended from a stationary or a portable type of hanger (not shown), the kit 10 being supported in this unfolded position near a bed or table in an emergency room. In the unfolded position of the kit 10, substantially all of the medical equipment retained therein is readily accessible for convenient use by medical personnel.

When the kit 10 is maneuvered to the folded position, the equipment retained therein is isolated from the outside environment surrounding the kit 10, thereby sealingly protecting such equipment from the effects of the surrounding environment. The equipment retained within the kit 10 is also protected from abuse, damage, and loss when the kit 10 is in the folded position.

Since a pack support frame like the pack support frame 12 is commercially available, a detailed description thereof is not deemed necessary. However, some of the major components of the pack support frame 12 will be described for the purpose of relating the kit 10 to the pack support frame 12.

The pack support frame 12 generally includes a frame member 14 (shown more clearly in FIGS. 2 and 3). As can be seen more clearly in FIG. 2, the frame member 14 is shaped to generally conform to the shape of a person's back. As can be seen more clearly in FIG. 3, the frame member 14 includes a plurality of rigid rods which are connected in a conventional manner such as via welding. The rods of the frame member 14 are preferably constructed of a light-weight material such as aluminum tubing, for example.

The frame member 14 has a right side portion 16 and a left side portion 18. In this instance, the right side portion 16 and the left side portion 18 are characterized as those portions of the frame member 14 which are positioned adjacent the right side and the left side, respectively, of a person carrying the emergency medical kit 10, in an assembled postion of the emergency medical kit 10 and the pack support frame 12.

The pack support frame 12 also has a waist belt 20 and right side and left side shoulder straps 22 and 24, respectively, which cooperate to removably attack the pack support frame 12 to a person's back. A pad 26 may also be utilized with the frame member 14 to cushion a person's back from the rigid members of the pack support frame 12.

A plurality of posts 28 are connected to the right side portion 16 and the left side portion 18 of the pack support frame 12. In one preferred embodiment, a set of four of the posts 28 are connected to the right side portion 16, and a corresponding set of four posts 28 are connected to the left side portion 18 for a total of eight of the posts 28. The posts 28 comprising each set thereof are spaced-apart in an equi-distant fashion along one of the left and the right side portions 16 and 18, each post 28 extending a distance transversely away from the pack support frame 12. A bore (not shown) is formed through each post 28, each bore being disposed generally parallel to its respective portion of the frame member 14. The bores on either side (i.e., right side or left side) of the frame member 14 are axially aligned in a slightly curved manner. The posts 28 are utilized to connect the kit 10 to the pack support frame 12, in a manner to be made more apparent below.

As shown more clearly in FIGS. 5 and 6, the emergency medical kit 10 generally includes a flexible sheet 30, having an outer peripheral edge 32 extending generally peripherally about the sheet 30 and substantially defining the outermost edge of the sheet 30 in the unfolded position of the kit 10. The kit 10, or more particularly, the sheet 30 has opposite first and second ends 34 and 36, respectively, and opposite first and second faces 38 and 40, respectively.

A portion of a holding assembly is connected to the sheet for removably holding the medical equipment in a position supported on the sheet. In the preferred embodiment, the holding assembly generally comprises a plurality of pockets and a plurality of straps. The pockets are formed and positioned on the first and second faces 38 and 40 of the sheet 30 in a predetermined fashion. The straps are connected to the first face 38 of the sheet 30. The pockets and straps are used to separately retain predetermined items of medical equipment in a readily accessible manner (the medical equipment not being shown in the drawings for clarity unless otherwise indicated). Each pocket and each strap will be specifically identified further below.

A plurality of continuous closure fasteners cooperates with the pockets and straps formed on and connected to the sheet, respectively, to retain medical equipment articles. In general, each pocket has a portion of the holding assembly connected thereto in a manner to be made more apparent below. The portion of the holding assembly associated with a specific pocket will be disclosed and specifically identified with the disclosure of the respective pocket.

The arrangement of the above identified pockets and straps and the manner in which the emergency medical kit 10 assumes the folded position or the unfolded position, cooperate to substantially divide the kit 10 into several distinct portions. That is, the emergency medical kit 10 in general and the sheet 30 in particular are further comprised of a first end portion 42 generally defining the first end 34, a second end portion 44 generally defining the second end 36, and a medial portion 46 disposed generally between the first end portion 42 and the second end portion 44. Even though the sheet 30 is constructed of one integral piece of material in the preferred embodiment, it will be described herein as the above identified portions 42, 22 and 46, it being understood that the sheet 30 could be constructed of several pieces connected to form the integral unit.

The first end portion 42 and the second end portion 44 are each hingedly connected to the medial portion 46 (the first and the second end portions 42 and 44 are each foldable with respect to the medial portion 46). That is, when the kit 10 is moved from the unfolded position to the folded position, the medial portion 46 moves relative to the first end portion 42, and the second end portion 44 moves relative to the medial portion 46 and the first end portion 42 as if the portions 42, 44 and 46 were connected via hinge elements. The portions of the sheet 30 defining these hinged or foldable connections are at least partially shown in the drawings as fold-lines, as will be described in greater detail below.

The division of the emergency medical kit 10 into the first end portion 42, the second end portion 44, and the medial portion 46 is more pronounced on the second face 40, as can be seen more clearly in FIG. 6. However, this division is also identifiable on the first face 38 via first and second fold-lines 48 and 50, respectively. The first fold-line 48 separates the first end portion 42 from the medial portion 46 and extends generally transversely across the sheet 30. The second fold-line 50 separates the second end portion 44 from the medial portion 46 and also extends transversely across the sheet 30 with the medial portion 46 being disposed between the first fold-line 48 and the second fold-line 50.

The kit 10 also includes a right side portion 42 and a left side portion 54 which, in one embodiment, are integrally formed with the first end portion 42. Furthermore, the right side portion 52 and the left side portion 54 are also hingedly connected to the first end portion 42 (that is, the right side portion 52 and the left side portion 54 are ach foldably connected to the first end portion 41), the hinged or foldable connections of the right side portion 52 and the left side portion 54 to the first end portion 42 being more clearly shown in FIG. 5. More particularly, the right side portion 52 is separated from the first end portion 42 via a third fold-line 56 extending from near the first end 34 to near the medial portion 46. Similarly, the left side portion 54 is separated from the first end portion 42 via a fourth fold-line 58 extending from near the first end 34 to near the medial portion 46. The third fold-line 56 and the fourth fold-line 58 are generally parallel and a medial portion of the first end portion 42 is disposed generally between the third and the fourth fold-lines 56 and 58.

A first pocket 60 is formed on the first face 38 of the sheet 30 near the first end 34 and generally adjacent the fourth fold-line 58. The first pocket 60 includes a cover 62 which is constructed of a flexible material. The cover 62 is connected to the sheet 30 in a conventional manner such as via stitching. A compartment (not shown) is formed between the cover 62 and the sheet 30. The cover 62 is connected to the sheet 30 such that an opening 64 is formed for providing access to the compartment from the outside environment surrounding the first pocket 60. The first pocket 60, in general, and the cover 62, in particular, extend longitudinally on the sheet 30 with the opening 64 facing toward the first end 34. The opening 64 substantially defines an open end of the first pocket 60 and a longitudinally opposite portion of the first pocket 60 defines a closed end of the first pocket 60, the first pocket 60 also having opposite sides 61 and 63.

Some of the medical equipment is retained within the compartment formed via the first pocket 60 in a readily accessible position in the unfolded position of the medical kit 10. In one preferred arrangement, the first pocket 60 is utilized to hold medical equipment such as bottles or bags containing intravenous fluids or the like.

A closure apparatus, such as a drawstring 66, is utilized in the preferred embodiment to retainingly seal or close the compartment for retaining the medical equipment within the compartment of the first pocket 60. More particularly, the drawstring 66 is connected to the cover 62, near the opening 64, in a conventional manner such as via stitching. The drawstring 66 has a closed position (shown more clearly in FIG. 5) and an open position (not shown). In the open position, the compartment formed via the first pocket 60 is accessible from the oustide environment surrounding the first pocket 60 via the opening 64. On the other hand, the compartment formed via the first pocket 60 is retainingly sealed or closed in the closed position of the drawstring 66. The medical equipment retained in the compartment formed via the first pocket 60 is substantially prevented from being accidentally displaced, or lost, while the compartment formed via the first pocket 60 is retainingly sealed or closed via the drawstring 66.

The drawstring 66 can be moved from the open position to the closed position (shown more clearly in FIG. 5) via pulling the loose ends of the drawstring 66 away from the opening 64. The opening 64 is thereby substantially closed. The opening 64 can thereafter be opened via a person inserting one of his hands through the opening 64 and into the compartment, and then spreading apart his fingers and causing enlargement of the opening 64. The drawstring 66 is thereby moved to the open position. The loose ends of the drawstring 66 may be tied together in the closed position, if desired in some applications.

A second pocket 68 is formed on the first end portion 42 of the first face 38 and positioned generally adjacent the first pocket 60. The second pocket 68 is constructed similar to the first pocket 60, and includes: a cover 51 constructed of a flexible material and connected to the sheet 30 in a manner forming a compartment (not shown); an opening 53 for providing access to the medical equipment retained within the compartment formed via the second pocket 68, the opening 53 defining an open end of the second pocket 68 and a longitudinally opposite portion of the second pocket 68 defining a closed end of the second pocket 68; and opposite sides 55 and 57. The second pocket 68 also includes a drawstring 59 closure apparatus for opening and closing the opening 53 of the second pocket 68 in a manner similar to that described before with respect to the drawstring 66 of the first pocket 60.

As can be seen more clearly in FIG. 5, the second pocket 68 is disposed upon the sheet 30 between the first pocket 60 and the third fold-line 56. The second pocket 68 is also utilized to retain medical equipment such as bottles or bags containing intravenous fluids or the like in a manner like that described before with respect to the first pocket 60.

A third pocket 70 is formed on the first end portion 42 of the first face 38 of the sheet 30 and positioned generally adjacent the third pocket 68. The third pocket 70 is constructed similar to the first and the second pockets 60 and 68, and the third pocket 70 generally includes: a cover 65 constructed of a flexible material and connected to the sheet 30 in a manner forming a compartment (not shown); an opening 67 for providing access to the medical equipment retained within the compartment formed via the third pocket 70, the opening 67 defining an open end of the third pocket 70 defining a closed end of the third pocket 70; and opposite sides 69 and 71. The third pocket 70 also includes a drawstring 73 closure apparatus for opening and closing the opening 67 of the third pocket 70 in a manner similar to that described before with respect to the drawstrings 66 and 59 of the first and the second pockets 60 and 68, respectively.

The third pocket 70 is disposed between the second pocket 68 and the third fold-line 56. In other words, the pockets 60, 68, and 70 are arranged on the first end portion 42 of the first face 38 of the sheet 30 in a side-by-side relationship. The third pocket 70 may also be utilized to retain medical equipment such as bottles or bags containing preselected fluid in a manner like that described before with respect to the first and the second pockets 60 and 68.

The side 63 of the first pocket 60 is disposed near the side 55 of the second pocket 68, the sides 63 and 55 being spaced a distance apart forming a first envelope pocket 72 on the sheet 30, the first envelope pocket 72 being formed generally between the first and the second pockets 60 and 68 and a portion of the sheet 30. The space between the sides 63 and 55 of the first and the second pockets 60 and 68 defines a compartment (not shown) formed between the sheet 30 and the first and the second pockets 60 and 68. The first envelope pocket 72 is shaped to retain medical equipment in a manner similar to the pockets 60, 68 and 70, described before.

A portion of a closure apparatus 74 is connected to the side 63 of the first pocket 68 and another portion of the closure apparatus 74 is connected to the side 55 of the second pocket 68. The closure apparatus 74 has an open position and a closed position, the closure apparatus 74 being shown in the closed position in FIG. 5. In the open position of the closure apparatus 74, the compartment formed via the space between the first and the second pockets 60 and 68 of the first envelope pocket 72 is accessible from the outside environment surrounding the first envelope pocket 72 via the opening formed between the sides 63 and 55 of the second pockets 60 and 68. In the closed position, the compartment formed via the space between the first and the second pockets 60 and 68 is retainingly sealed or closed and medical equipment retained therein is substantially prevented from accidental displacement, or loss, from the compartment of the first envelope pocket 72. The closure apparatus 74 may be a conventional zipper type assembly or an assembly of corresponding Velcro strips, for example. Velcro is the trade name for a fastener providing a continuous closure type of seal. A given assembly of Velcro strips generally includes one strip comprised of "hooks", and another strip comprised of "loops" and, when the two strips are passed together, such strips join to form a slip-proof connection.

The side 57 of the second pocket 68 is disposed near the side 69 of the third pocket 70, the sides 57 and 69 being spaced a distance apart forming a second envelope pocket 76, similar to the first envelope pocket 72. In other words, the second envelope pocket 76 is formed generally between the second and third pockets 68 and 70 and a portion of the sheet 30. The space between the sides 57 and 69 of the second and third pockets 68 and 70 defines a compartment (not shown) formed between the sheet 30 and the second and third pockets 68 and 70. The second envelope pocket 76 is shaped to retain medical equipment in a manner similar to the first envelope pocket 72, described before.

A portion of a closure apparatus 75, similar to the closure apparatus 74, is connected to the side 57 of the second pocket 68 and another portion of the closure apparatus 75 is connected to the side 69 of the third pocket 70. The closure apparatus 75 is utilized to retainingly seal the second envelope pocket 76 in a manner similar to that of the closure apparatus 74 retainingly sealing the first envelope pocket 72.

A first flap top pocket 78 is formed on the first end portion 42 of the sheet 30 generally between the first and second pockets 60 and 68 and the first fold-line 48. More particularly, the first flap top pocket 78 is disposed generally adjacent the first and second pockets 60 and 68 and generally adjacent a portion of the fourth fold-line 58. The first flap top pocket 78 generally includes a cover 80 constructed of a flexible material, the cover 80 being connected to the sheet 30 in a conventional manner such as via stitching, for example. A compartment (not shown) is formed between the sheet and the cover 80. Also, an opening (not shown) is formed through the cover 80 providing access to the compartment from the outside environment surrounding the first flap top pocket 78. The opening defines an open first end of the first flap top pocket 78 and a portion thereof opposite the open first end defines a closed second end of the first flap top pocket 78. The first flap top pocket 78 also has opposite sides 77 and 79 which extend between the open first end and the closed second end thereof.

A cover flap 82 is hingedly, or foldably, connected with the cover 80 to the sheet 30, the cover flap 82 being utilized to selectively close the opening formed via the cover 80. In other words, the opening providing access to the compartment of the first flap top pocket 78 is disposed immediately adjacent the closed ends of the first and second pockets 60 and 68 with the cover flap 82 being disposed therebetween.

The cover flap 82 is another type of closure apparatus and the cover flap 82 has an open position and a closed position. The compartment formed via the cover 80 is accessible from the outside environment surrounding the first flap top pocket 78 via the opening formed therethrough in the open position of the cover flap 82. In the closed position of the cover flap 82, the compartment is retainingly sealed or closed and the medical equipment retained therein thus is prevented from displacement therefrom. The cover flap 82 may be maintained in the closed position via the use of corresponding Velcro strips (not shown). In one embodiment for example, a Velcro strip comprised of "hooks" could be connected to the underside of the cover flap 82, and a Velcro strip comprised of "loops" could be connected to a corresponding portion of the cover 80 near the opening. The pocket 82 is preferably utilized to retain medical equipment such as syringes and alcohol swabs, for example.

A second flap top pocket 84 is formed on a medial portion of the first end portion 42 of the sheet 30. More particularly, the second flap top pocket 84 is disposed between the first flap top pocket 78 and the third fold-line 56 in transverse alignment with the first flap top pocket 78. The second flap top pocket 84 is utilized to retain medical equipment such as adhesive tape, for example.

The second flap top pocket 84 is constructed similar to the first flap top pocket 78 and generally includes: a cover 85 constructed of a flexible material, the cover 85 being connected to the sheet 30 in a conventional manner such as via stitching, for example. A compartment (not shown) is formed between the sheet 30 and the cover 85. An opening (not shown) is formed through the cover 85 providing access to the compartment from the outside environment surrounding the second flap top pocket 84. The opening defines an open first end of the second flap top pocket 84 and a portion thereof opposite the open first end defines a closed second end of the second flap top pocket 84. The second flap top pocket 84 also has opposite sides 81 and 83 which extend between the open first end and the closed second end thereof.

A cover flap 87 is hingedly, or foldably, connected with the cover 85 to the sheet 30, the cover flap 87 being utilized to selectively close the opening formed via the cover 85, in a manner similar to that of the cover flap 82 closing the opening formed via the first flap top pocket 78.

The side 79 of the first flap top pocket 78 is disposed near the side 81 of the second flap top pocket 84, the sides 79 and 81 being spaced a distance apart forming a third envelope pocket 86 on the sheet 30. That is, the third envelope pocket 86 is formed generally between the first and second flap top pockets 78 and 84 and a portion of the sheet 30. The space between the sides 79 and 81 of the first and the second flap top pockets 78 and 84 defines a compartment (not shown) formed between the sheet 30 and the first and second flap top pockets 78 and 84. The third envelope pocket 86 is shaped to retain medical equipment in a manner similar to that of the first and second envelope pockets 72 and 76.

A portion of a closure apparatus 89, similar to the closure apparatus 74 and 75, is connected to the side 79 of the first flap top pocket 78 and another portion of the closure apparatus 89 is connected to the side 81 of the second flap top pocket 84. The closure apparatus 89 is utilized to retainingly seal the third envelope pocket 86 in a manner similar to that of the closure apparatus 74 and 75 retainingly sealing the first and second envelope pockets 72 and 76, respectively.

A third flap top pocket 88 is formed generally on the medial portion 46 of the first face 38 of the sheet 30. More particularly, the third flap top pocket 88 extends transversely approximately one-half the distance across the sheet 30 with the depth thereof extending from immediately adjacent the closed second end of the first flap top pocket 78 to near the first fold line 48. The third flap top pocket 88 may be utilized to retain medical equipment such as a laryngeale scope and blades, for example.

The third flap top pocket 88 is also constructed similar to the first flap top pocket 78 and generally includes: a cover 91 constructed of a flexible material, the cover 91 being connected to the sheet 30 in a conventional manner such as via stitching, for example. A compartment (not shown) is formed between the sheet 30 and the cover 91. An opening (not shown) is formed through the cover 91 providing access to the compartment from the outside environment surrounding the third flap top pocket 88. The opening defines an open first end of the third flap top pocket 88 and a portion thereof opposite the open first end defines a closed second end of the third flap top pocket 88. The third flap pocket 88 also has opposite sides which extend between the open first end and the closed second end thereof.

A cover flap 93 is hingedly, or foldably, connected with the cover 91 to the sheet 30, the cover flap 93 being utilized to selectively close the opening formed via the cover 91, in a manner similar to that of the cover flap 82 closing the opening formed via the first flap top pocket 78.

A fourth flap top pocket 90 is formed on a medial portion 46 of the first face 38 of the sheet 30 immediately adjacent the second flap top pocket 84, in one aspect, and, in another aspect, immediately adjacent the third flap top pocket 88. In other words, the third and fourth flap top pockets 88 and 90 are in transverse alignment extending across the width of the medial portion 46 of the sheet 30. Furthermore, the fourth flap top pocket 90 is disposed generally between the closed second end of the second flap top pocket 84 and the first fold line 48. The fourth flap top pocket 90 is utilized to retain any desired miscellaneous medical equipment.

The fourth flap top pocket 90 is also constructed similar to the first flap top pocket 78 and generally includes: a cover 95 constructed of a flexible material, the cover 95 being connected to the sheet 30 in a conventional manner such a via stitching, for example. A compartment (not shown) is formed between the sheet 30 and the cover 95 providing access to the department from the outside environment surrounding the fourth flap top pocket 90. The opening defines an open first end of the fourth flap top pocket 90 and a portion thereof opposite the open first end defines a closed second end of the fourth flap top pocket 90. The second flap top pocket 90 also has opposite sides which extend between the open first end and the closed second end.

A cover flap 97 is hingedly, or foldably, connected with the cover 95 to the sheet 30, the cover flap 97 being utilized to selectively close the opening formed via the cover 95, in a manner similar to that of the cover flap 82 closing the opening formed via the first flap top pocket 78.

A fifth flap top pocket 92, similar in construction to the first flap top pocket 78, is formed on the first face 38 of the left side portion 54 near the first end 34. More particularly, the fifth flap top pocket 92 extends transversely across the width of the left side portion 54, in one aspect, and, in another aspect, extends longitudinally on the left side portion 54 from near the first end 34 to a medial portion of the left side portion 54. The fifth flap top pocket 92 may be utilized to retain medical equipment such as boxes containing drugs, for example.

The fifth flap top pocket 92 generally includes: a cover 99 constructed of a flexible material, the cover 99 being connected to the sheet 30 in a conventional manner such as via stitching, for example. A compartment (not shown) is formed between the sheet 30 and the cover 99. An opening (not shown) is formed through the cover 85 providing access to the compartment from the outside environment surrounding the fifth flap top pocket 92. The opening defines an open first end of the fifth flap top pocket 92 and an opposite portion of the fifth flap top pocket 92 defines a closed end thereof. The fifth flap top pocket 92 also has opposite sides extending between the open first end and the closed second end.

A cover flap 101 is hingedly, or foldably, connected with the cover 99 to the sheet 30, the cover flap 101 being utilized to selectively close the opening formed via the cover 99, in a manner similar to that of the cover flap 82 closing the opening formed via the first flap top pocket 78.

A fourth pocket 94, similar to the first pocket 60, is formed on the left side portion 54 generally between the closed second end of the fifth flap top pocket 92 and a corner portion of the outer peripheral edge 44. The fourth pocket 94 includes: a cover 103 constructed of a flexible material and connected to the sheet 30 in a manner forming a compartment (not shown); an opening 105 for providing access to the medical equipment retained within the compartment formed via the fourth pocket 94, the opening 105 defining an open first end of the fourth pocket 94 and a longitudinally opposite portion of the fourth pocket 94 defining a closed second end thereof; and opposite sides extending between the open first end and the closed second end. The fourth pocket 94 also includes a drawstring 107 closure apparatus for opening and closing the opening 105 of the fourth pocket 94 in a manner similar to that described before with respect to the drawstring 66 of the first pocket 60.

The opening associated with the fourth pocket 94 is disposed immediately adjacent the closed end of the fifth flap top pocket 92 with the fourth pocket 94 extending a distance longitudinally therefrom in a direction generally toward the second end 36 of the kit 10, the fourth pocket 94 being spaced a predetermined distance away from the fourth fold line 58. Even though the fourth pocket 94 is constructed similarly to the first pocket 78, the fourth pocket 94 is slightly smaller in physical dimension than the first pocket 78. The fourth pocket 94 is utilized to retain medical equipment such as sodium bicarbonate, for example.

A sixth flap top pocket 96 is formed on a medial portion of the left side portion 54 generally between a portion of the fourth fold line 58 and a portion of the fourth pocket 94 (near the open first end thereof) and immediately adjacent the closed second end of the fifth flap top pocket 92. The sixth flap top pocket 96 may be utilized to retain medical equipment such as needles, for example.

The sixth flap top pocket 96 is constructed similar to, but is physically smaller than, the first flap top pocket 78 and generally includes: a cover 109 constructed of a flexible material, the cover 109 being connected to the sheet 30 in a conventional manner such as via stitching, for example. A compartment (not shown) is formed between the sheet 30 and the cover 109. An opening (not shown) is formed through the cover 109 providing access to the compartment from the outside environment surrounding the sixth flap top pocket 96. The opening defines an open first end of the sixth flap top pocket 96 and a portion of the sixth flap top pocket 96 opposite the open first end thereof defines a closed second end of the sixth flap top pocket 96. The sixth flap top pocket 96 also has opposite first and second sides extending between the open first end and the closed second end thereof.

A cover flap 111 is hingedly, or foldably, connected with the cover 109 to the sheet 30, the cover flap 111 being utilized to selectively close the opening formed via the cover 109, in a manner similar to that of the cover flap 82 closing the opening formed via the first flap top pocket 78.

A seventh flap top pocket 98 is formed on a corner of the left side portion 54 between the closed end of the fourth pocket 94 and an end portion of the fourth fold line 58, in one aspect, and, in another aspect, between the sixth flap top pocket 96 and an inside corner portion of the outer peripheral edge 44. The seventh flap top pocket 98 may be utilized to retain any miscellaneous medical equipment.

The seventh flap top pocket 98 is constructed similar to the first flap top pocket 78 and is similar in physical dimension to the sixth flap top pocket 96, and generally includes: a cover 113 constructed of a flexible material, the cover 113 being connected to the sheet 30 in a conventional manner such as via stitching, for example. A compartment (not shown) is formed between the sheet 30 and the cover 113 providing access to the compartment from the outside environment surrounding the seventh flap top pocket 98. The opening defines an open first end of the seventh flap top pocket 98 and a portion of the seventh flap top pocket 98 opposite the open first end thereof defines a closed second end of the seventh flap top pocket 98. The seventh flap top pocket 98 also has opposite sides which extend between the open first end and the closed second end thereof.

A cover flap 115 is hingedly, or foldably, connected with the cover 113 to the sheet 30, the cover flap 113 being utilized to selectively close the opening formed via the covers 113, in a manner similar to that of the cover flap 82 closing the opening formed via the first flap top pocket 78.

An eighth flap top pocket 100 is formed on the right side portion 52 near the first end 34 and extends generally between a corner portion of the outer peripheral edge 44 and the third fold line 56. The eighth flap top pocket 100 may be utilized to retain medical equipment such as boxes containing drugs, for example.

The eighth flap top pocket 100 is constructed similar to the first flap top pocket 78 and generally includes: a cover 117 constructed of a flexible material, the cover 117 being connected to the sheet 30 in a conventional manner such as via stitching, for example. A compartment (not shown) is formed between the sheet 30 and the cover 117. An opening (not shown) is formed through the cover 117 for providing access to the compartment from the outside environment surrounding the eighth flap top pocket 100. The opening defines an open first end of the eighth flap top pocket 100 and a portion of the eighth flap top pocket 100 opposite the open first end thereof defines a closed second end of the eighth flap top pocket 100.

A cover flap 119 is hingedly, or foldably, connected with the cover 117 to the sheet 30, the cover flap 119 being utilized to selectively close the opening formed via the cover 117, in a manner similar to that of the cover flap 82 closing the opening formed via the first flap top pocket 78.

A fifth pocket 102, similar in construction to the first pocket 60, and similar in physical dimension to the fourth pocket 94, is formed on a corner portion of the right side portion 52 generally between the closed end of the eighth flap top pocket 100 and a corner portion of the outer peripheral edge 44. More particularly, the fifth pocket 102 is spaced apart a predetermined distance from the third fold line 56. The fifth pocket 102 is utilized to retain medical equipment such as sodium bicarbonate or other prefilled drugs, for example.

The fifth pocket 102 includes: a cover 121 constructed of a flexible material and connected to the sheet 30 in a manner forming a compartment (not shown); an opening 123 for providing access to the medical equipment retained within the compartment formed via the cover 121, the opening 123 defining an open first end of the fifth pocket 102 and a longitudinally opposite portion of the fifth pocket 102 defining a closed end of the fifth pocket 102; and opposite sides formed between the open first end and the closed second end. The fifth pocket 102 also includes a drawstring 125 closure apparatus for opening and closing the opening 123 of the fifth pocket 102 in a manner similar to that described before with respect to the drawstring 66 of the first pocket 60.

A ninth flap top pocket 104, similar in construction to the first flap top pocket 78, and similar in physical dimension to the sixth flap top pocket 96, is formed on a medial portion of the right side portion 52 between a medial portion of the third fold line 56 and a portion of the fifth pocket 102 (near the open end thereof), in one aspect, and, in another aspect, between the closed end of the eighth flap top pocket 100 and a right end portion of the first fold line 48. The ninth flap top pocket 104 may be utilized to retain medical equipment such as needles, for example.

The ninth flap top pocket 104 generally includes: a cover 127 constructed of a flexible material, the cover 127 being connected to the sheet 30 in a conventional manner such as via stitching, for example. A compartment (not shown) is formed between the sheet 30 and the cover 127. An opening (not shown) is formed through the cover 127 providing access to the compartment from the outside environment surrounding the ninth flap top pocket 104. The opening defines an open first end of the ninth flap top pocket 104 and a portion of the ninth flap top pocket 104 opposite the open first end thereof defines a closed second end of the ninth flap top pocket 104. The second flap top pocket 104 also has opposite sides which extend between the open first end and the closed second end.

A cover flap 129 is hingedly, or foldably, connected with the cover 127 to the sheet 30, the cover flap 129 being utilized to selectively close the opening formed via the cover 127, in a manner similar to that of the cover flap 82 closing the opening formed via the first flap top pocket 78.

A tenth flap top pocket 106, similar in construction to the first flap top pocket 78 and similar in physical dimension to the sixth flap top pocket 96, is formed on a corner portion of the right side portion 52 between an end portion of the third fold line 56 and a closed end of the fifth pocket 102, in one aspect, and, in another aspect, between the right end of the first fold line 48 and the closed end of the ninth flap top pocket 104. The tenth flap top pocket 106 may be utilized to retain any desired miscellaneous medical equipment.

The tenth flap top pocket 106 generally includes: a cover 131 constructed of flexible material, the cover 131 being connected to the sheet 30 in a conventional manner such as via stitching, for example. A compartment (not shown) is formed between the sheet 30 and the cover 131. An opening (not shown) is formed through the cover 131 providing access to the compartment from the outside environment surrounding the tenth flap top pocket 106. The opening defines an open first end of the tenth flap top pocket 106 and a portion of the tenth flap top pocket 106 opposite the open first end thereof defines a closed second end of the tenth flap top pocket 106.

A cover flap 133 is hingedly, or foldably, connected with the cover 131 to the sheet 30, the cover flap 133 being utilized to selectively close the opening formed via the cover 131, in a manner similar to that of the cover flap 82 closing the opening formed via the first flap top pocket 78.

A first plurality of straps 108 (only two of the straps 108 being identified via a reference numeral in FIG. 5 for clarity) are connected to the second end portion 44 of the first face 38 of the sheet 30 generally near the second fold-line 50, the straps 108 extending in a direction generally transversely across the second end portion 44. Each strap 108 cooperates with an adjacent portion of the first face 38 of the sheet 30 to form a space (not shown) generally between the respective strap 108 and the first face 38 of the sheet 30. In one preferred embodiment, the kit 10 includes eight (8) of the straps 108 and each strap 108 cooperates with the adjacent portion of the sheet 30 to removably retain an article of medical equipment on the first face 38 of the sheet 30 in a readily accessible manner. The straps 108 may be utilized to retain medical equipment such as oral airways 110, for example (only two of the airways 110 being designated via a reference numeral in FIG. 5 for example). In one preferred embodiment, the straps 108 are formed via fastening a single piece of material or strap at predetermined, spaced-apart positions on the first face 38 of the sheet 30 in a manner to form the desired number of spaces. It is preferred that this material be an elastic or flexible type of material to further facilitate in removably retaining medical equipment (such as the oral airways 110) in a readily accessible manner.

A plurality of pockets 112 are formed in a layered fashion transversely across a medial portion of the second end portion 44, the pockets 112 being staggered one upon another. Each of the pockets 112 is generally similar in construction to the first flap top pocket 78. However, in the case of the pockets 112, the depth thereof extends transversely across the width of the sheet 30, as opposed to the depth of a pocket such as the first flap top pocket 78 extending longitudinally across the sheet 30.

Each pocket 112 is formed via the connection of a cover constructed of flexible material to a portion of the sheet 30. In one preferred embodiment, five (5) of the pockets 112 are formed comprising the covers 145, 147, 149, 151, and 153. The covers 145, 147, 149, 151, and 153 are each only partially shown in FIG. 5.

The cover 145 is connected to a portion of the first face 38 of the sheet 30 with a compartment (not shown) formed between the cover 145 and the adjacent portion of the sheet 30, the compartment retaining predetermined articles of medical equipment. An opening (not shown) is formed for providing access to the compartment from the outside environment surrounding the pocket 112 formed via the cover 145. The opening defines an open first end of the pocket 112 formed via the cover 145 with an opposite portion thereof defining a closed second end.

A cover flap 155 is hingedly, or foldably, connected to the sheet 30 adjacent the opening formed via the cover 145. The cover flap 155 is utilized to selectively close the opening whereby the compartment formed via the cover 145 is retainingly sealed, in a manner similar to that of the cover flap 82 closing the opening and retainingly sealing the compartment formed via the first flap top pocket 78.

The cover 147 is connected to the sheet 30 and over a portion of the cover 145. A compartment (not shown) is formed between the covers 145 and 147, the compartment being utilized to retain predetermined articles of medical equipment. An opening (not shown) is formed for providing access to the compartment formed between the covers 145 and 147. A cover flap 157 is connected to the cover 145 adjacent the opening formed via the cover 147. The cover flap 157 is utilized to selectively close the opening formed via the cover 147 whereby the compartment formed via the cover 147 is retainingly sealed in a manner similar to that of the cover flap 155 in regard to the cover 145.

The covers 149, 151, and 153 are connected to the sheet 30 over portions of the covers 147, 149, and 151, respectively, in a manner similar to that of the cover 147 being connected to the sheet 30 over a portion of the cover 145. Likewise, a compartment is formed between the covers 148 and 149, the covers 149 and 151, and the covers 151 and 153, in a manner similar to that of the compartment formed between the covers 145 and 147. Openings (not shown) are also formed providing access to the compartments formed via the covers 149, 151 and 153 in a manner similar to that of the opening formed via the covers 147.

Cover flaps 159, 161, and 163 are connected to the covers 147, 149, and 151, respectively, adjacent the openings formed via the covers 149, 151, and 153, respectively. The cover flaps 159, 161, and 163 are utilized to selectively close the openings formed via the covers 149, 151, and 153 thereby retainingly sealing the compartments formed via the covers 149, 151, and 153, respectively, in a manner similar to that of the cover flap 157 in regard to the cover 147.

As shown more clearly in FIGS. 5, 6, 7, and 8, a flap 118 is hingedly connected transversely across a portion of the second end portion 44 near the second end 36. The flap 118 has a closed or folded position (shown more clearly in FIGS. 5 and 6) and the flap 118 also has an opened or unfolded position (shown more clearly in FIGS. 7 and 8). The flap 118 is constructed of a piece of flexible material and one end of the flap 118 is connected to the first face 38 of the sheet 30, such as via stitching, for example, the opposite end of the flap 118 being folded over such that the piece of material forming the flap 118 is approximately folded in half. The half-portions of the piece of material forming the flap 118 are connected along their outer peripheral edges, such as via stitching, for example, with the portions of the flap 118 near each end being left unconnected so as to form a compartment (not shown) between the two half-portions of the piece of material forming the flap 118. An opening (not shown) is formed between the two half-portions of the piece of material forming the flap 118 for providing access to the compartment formed therebetween. The flap 118 is further characterized as having a first or outer face 120, and a second or inner face 122. In other words, when the flap 118 is in the closed position and the emergency medical kit 10 is in the unfolded position (as is shown in FIG. 5), the outer face 120 is facing away from the sheet 30, and when the flap 118 is in the open position and with the kit 10 in the unfolded position, the inner face 122 is facing away from the sheet 30, as shown more clearly in FIGS. 7 and 8. The compartment formed via the flap 118 is utilized to retain medical equipment such as a stethoscope, for example.

A second plurality of straps 124, and a third plurality of straps 126, similar to the first plurality of straps 108, are connected to corresponding portions of the inner face 122 of the flap 118. Only two of the straps 124 and two of the straps 126 are identified via a reference numeral in FIG. 7. More particularly, the second and third plurality of straps 124 and 126, respectively, extend across the inner face 122 of the flap 118 and are disposed in a generally parallel, spaced-apart relationship.

Each strap 124 or 126 cooperates with an adjacent portion of the inner face 122 of the flap 118 to form a space 128 generally between the respective strap 124 or 126 and the inner face 122 of the flap 118. Only two of the spaces 128, formed via two of the straps 124, are shown in FIG. 8. In one preferred embodiment, the kit 10 includes five (5) of the straps 124 and five (5) of the straps 126. Each strap 124 or 126 cooperates with an adjacent portion of the flap 118 to removably retain a predetermined article of medical equipment in a readily accessible manner. The straps 124 and 126 may be utilized to retain medical equipment such as endotracheal tubing 130, for example. Only two endotracheal tubes 130 are identified via a reference numeral in FIG. 7.

In one preferred embodiment, the straps 124 and 126 are formed via fastening a single piece of material, or strap, at predetermined, spaced-apart positions on the inner face 122 of the flap 118 in a manner to form the desired number of spaces. It is preferred that this material be an elastic or flexible type of material to further facilitate in removably retaining medical equipment (such as the endotracheal tubing 30) in a readily accessible manner.

A fourth plurality of straps 132 and a fifth plurality of straps 134, also similar in construction to the first plurality of straps 108, are connected to corresponding portions of the second end portion 44 between the pockets 112 and the connection of the flap 118 to the first face 38 of the sheet 30. Only two of the straps 132 and two of the straps 134 are identified via a reference numeral in FIG. 7. The fourth and fifth straps 132 and 134 are covered via the flap 118 in the folded position of the flap 118. In the unfolded position of the flap 118, and the unfolded position of the kit 10, the straps 132 and 134 are substantially exposed to view and are accessible. The fourth and fifth straps 132 and 134 extend longitudinally (in relation to the sheet 30) and are spaced apart a predetermined distance in a parallel relationship. When the flap 118 is in the closed position, the second straps 124 are in contact with the fourth straps 132, and the third straps 126 are in contact with the fifth straps 134. Closure apparatus (not shown) such as Velcro strips are connected to each of the pluralities of straps 132 and 134, and 124 and 126, respectively, whereby the flap 118 may be maintained in the closed position. That is, strips of Velcro comprising "loops" could be connected to portions of the straps 132 and 134 and corresponding strips of Velcro comprising "hooks" could be connected to portions of the straps 124 and 128. Thereby, when the flap 118 is moved to the folded position and pressed against the sheet 30, the Velcro strip connected to the straps 124 is joined with the corresponding Velcro strip connected to the straps 132, and, similarly, the Velcro strip connected to the straps 126 is joined with the corresponding Velcro strip connected to the straps 134.

Each strap 132 or 134 cooperates with an adjacent portion of the first face 38 of the sheet 30 to form a space 136 generally between the respective strap 132 or 134 and the sheet 30. Only two of the spaces 136, formed via two of the strips 132, are shown in FIG. 8. In one preferred embodiment, the kit 10 includes six (6) of the straps 132 and six (6) of the straps 134. Each strap 132 or 134 cooperates with an adjacent portion of the sheet 30 to removably retain a predetermined article of medical equipment such as tubing components 138. Only two of the tubing components 138 are identified via a reference numeral in FIG. 7.

In one preferred embodiment, the straps 132 and 134 are each formed via fastening a single piece of material, or strap, at a predetermined, spaced-apart position on the sheet 30 in a manner to form the desired number of spaces. It is preferred that this material be an elastic or flexible type of material to further facilitate in removably retaining medical equipment (such as the tubing 138) in a readily accessible manner.

A first strap assembly 140 and a similar second strap assembly 142 are each connected to respective portions of the first face 38 of the second end portion 44 near the second end 36. The first strap assembly 140 is spaced a distance from the second strap assembly 142. More particularly, the first strap assembly 140 is generally comprised of a first strap member 144 and a similar second strap member 146. The second strap assembly 142 is generally comprised of a third strap member 148 and a fourth strap member 150 which are similar to the strap members 144 and 146, respectively. The first and second strap assemblies 140 and 142 each have a closed position (shown in FIGS. 5, 6 and 8) and an open position (not shown). When the first strap assembly 140 or the second strap assembly 142 is in the closed position, a space is formed between the first strap assembly 140 or the second strap assembly 142 and a portion of the first face 38. Predetermined articles of medical equipment are removably retained in the space cooperatively formed via the first and second strap assemblies 140 and 142 in the closed position thereof. In one use of the first and second strap assemblies 140 and 142, boxes 152 containing medical equipment are retained in the space against the first face 38 of the sheet 30.

One end of each of the strap members 144, 146, 148 and 150 is specifically connected to the first face 38 of the sheet 30, as can be seen partially in FIGS. 6 and 8. The opposite end, or loose end, of each strap member 144, 146, 148 and 150 has a portion of a connecting apparatus connected thereto for joining with the loose end of a corresponding strap member. THat is, the loose end of the strap member 144 is selectively connectable to the loose end of the strap member 146; and the loose end of the strap member 148 is selectively connectable to the loose end of the strap member 150.

In one preferred embodiment, corresponding portions of Velcro strips 154 are connected to the respective loose ends of the straps 144, 146, 148 and 150 to facilitate connections therebetween. The first and second strap assemblies 140 and 142 are thereby maintained in the closed position.

As shown in FIGS. 1 and 6, a pocket 156 is formed on the second face 40 of the medial portion 46 of the sheet 30 the pocket 156 substantially encompassing the medial portion 46. The pocket 156 generally includes a cover 158 constructed of flexible material which is connected to the second face 40 of the medial portion 46 of the sheet 30. A compartment (not shown) is formed between the second face 40 of the sheet 30 and the cover 158. An opening (not shown) is formed through the cover 158 for providing access to the compartment from the outside environment surrounding the emergency medical kit 10. In one preferred form, a conventional double zipper assembly 160 is connected to the cover 158 generally around the opening formed therethrough for providing a selectively closable opening. The double zipper assembly 160 has a closed position and an open position. In the closed position, medical equipment, which is retained in the compartment formed via the cover 158, is retainingly sealed therein. In the open position, access is provided to the compartment formed via the cover 158. The pocket 156 is utilized to retain medical equipment, such as surgical dressings or oxygen cylinders, for example.

As shown more clearly in FIGS. 2 and 8, a pocket 162 is formed on the second face 40 of the second end portion 44 near the second end 36. The pocket 162 is constructed similar to the pocket 156 and the pocket 162 generally includes a cover 164 constructed of flexible material which is connected to a portion of the second face 40 of the sheet 30. A compartment (not shown) is formed between the cover 164 and an adjacent portion of the sheet 30. An opening (not shown) is formed through a portion of the cover 164 for providing access to the compartment. The opening is selectively closable via a double zipper assembly 166 connected to the cover 164 generally around the opening formed through the cover 164. The double zipper assembly 166 is constructed similarly to the double zipper assembly 160, and has a closed position, whereby medical equipment retained via the cover 164 is retainingly sealed therein; and an open position, whereby medical equipment retained therein is readily accessible form the outside environment surrounding the pocket 162. Medical equipment, such as ventilation equipment, for example, is retained via the pocket 162.

A pocket 168 is formed on the second face 40 of the second end portion 44 of the sheet 30 generally between the pocket 162 and the second fold-line 50. The pocket 168 is similar in construction to the pocket 162. The pocket 168 generally includes of a cover 170 constructed of a flexible material which is connected to the second face 40 of the sheet 30 in a conventional manner, such as via stitching, for example. A compartment (not shown) is formed between the sheet 30 and the cover 170. Some of the medical equipment is retained within this compartment. An opening (not shown) is formed through a portion of the cover 170 for providing access to the compartment. The opening is selectively closable via a double zipper assembly 172, which is constructed similar to the double zipper assembly 160. This double zipper assembly 172 has an open position wherein any medical equipment retained via the cover 170 is readily accessible from the outside environment surrounding the pocket 168, and a closed position wherein any medical equipment retained via the cover 170 is retainingly sealed. The pocket 168 is utilized to retain medical equipment such as air splints or cervical collars, for example.

A pocket 174 is formed on the second face 40 of the sheet 30, the pocket 174 substantially encompassing the right side portion 52. The pocket 174 is constructed similar to the pocket 156 formed on the second face 40 of the medial portion 46. The pocket 174 generally includes a cover 176 constructed of flexible material which is connected to the sheet 30. A compartment (not shown) is formed between the cover 176 and the sheet 30. An opening (not shown) is formed through a portion of the cover 176 for providing access to the compartment. A double zipper assembly 178, which is constructed similar to the double zipper assembly 160, is utilized to selectively close the opening. The double zipper assembly 178 has an open position and a closed position. In the open position, the compartment formed via the cover 176 and any medical equipment retained therein are accessible from the outside environment surrounding the pocket 174. In the closed position, any medical equipment retained in the compartment is retainingly sealed. Medical equipment such as surgical dressings and oxygen cylinders, for example, is retainingly sealed and provided in a removably accessible manner via the pocket 174.

A pocket 180, similar to the pocket 174 formed on the second face 40 of the right side portion 52, is formed on the second face 40 of the left side portion 54. The pockets 174 and 180 are similar in construction and physical dimension. The pocket 180 is generally comprised of a cover 182 of flexible material connected to the sheet 30. The connection of the cover 182 to the sheet 30 forms a compartment (not shown) therebetween. An opening (not shown) is formed through a portion of the cover 182 for providing access to the compartment from the outside environment surrounding the pocket 180. The opening formed through the cover 182 is selectively closable via a closure apparatus such as a double zipper assembly 184 (similar to the double zipper assembly 160), for example. The pocket 180 is utilized to retain medical equipment such as surgical dressings and oxygen cylinders, for example.

A double zipper assembly 186, similar in construction to double zipper assembly 184, for example, is connected around the outer peripheral edge 32 of the sheet 30. The double zipper assembly 186 is utilized to maintain the emergency medical kit 10 in the closed position, when desired.

A first handle 188 is connected to the first end 34 of the sheet 30, and a similarly constructed second handle 190 is connected to the second end 36 of the sheet 30. In one manner, the first and second handles 188 and 190 may be utilized to transport the medical kit 10 by hand. In another manner, the first handle 188 may be utilized to suspend the kit 10 from a mobile hanger, or the like, for use in a hosiptal emergency room, for example.

Referring to FIG. 4, a plurality of rings 192 are connected to the second face 40 of the sheet 30 generally along the third fold line 56 and the fourth fold line 58. In the preferred embodiment, four (4) of the rings 192 are connected along the third fold line 56, and four (4) of the rings 192 are connected along the fourth fold line 58, for a total of eight (8) of the rings 192. The rings 192 are utilized to removably connect the emergency medical kit 10 to the pack support frame 12. More particularly, each ring 192 is disposed over one of the posts 28 connected to the pack support frame 14, as can be seen more clearly in FIG. 3. After the rings 192 have all been disposed over their respective posts 28, a retainer rod 194 is inserted through the bores formed through each set of the posts 28. The rings 192 are thereby substantially locked in place over the posts 28, as would be obvious to one skilled in the art.

Referring again to FIG. 4, a right side shoulder strap 196 and a similarly constructed left side shoulder strap 192 are connected to the second face 40 of the sheet 30. The shoulder straps 196 and 198 are, in turn, similarly constructed to the shoulder straps 22 and 24, respectively, connected to the pack support frame 14.

The right side shoulder strap 196 is connected at one end thereof to a portion of the sheet 30 near the first handle 188 and also near the third fold line 56. The other end of the right side shoulder strap 196 is connected to the second face 40 of the medial portion 46 adjacent the third fold line 56.

The left side shoulder strap 198 has one end thereof connected to the first end 34 of the sheet 30 near the fourth fold line 58 and also near the first handle 188. The other end of the left side shoulder strap 198 is connected to the second face 40 of the medial portion 46 adjacent the fourth fold line 58, directly opposite the corresponding end of the right side strap 196. The shoulder straps 196 and 198 are selectively adjustable via buckles 200, and may be utilized to removably attach the emergency medical kit 10 to a person's back in case the pack support frame 14 is not used.

Changes may be made in the construction and arrangement of the parts or the elements of the preferred embodiment as described herein without departing from the spirit and scope of the invention as defined in the following claims.

What is claimed is:
1. A medical kit supportable on the back of a person and holding medical kit equipment members, the medical kit comprising:
   a flexible sheet member having a first end and a second end, an outer peripheral edge, and a first face and a second face, the sheet member having an unfolded position wherein the first end is disposed generally away from the second end and the first face is exposed, and having a folded position wherein the first end and the second end are positioned in close spatial relationship to each other;
   holding means comprising a plurality of flexible compartment pockets connected to the sheet for removably holding and protecting a plurality of medical kit members in a predetermined position so that portions of the medical kit members are accessible when the sheet is positioned in the unfolded position and other portions of the medical kit members are accessible when the sheet is positioned in the folded position, the holding means comprising: a plurality of flexible covers forming with
      the sheet member a plurality of compartments, each compartment having an opening for providing access to the respective compartment, a portion of the medical kit members being retained within each of the compartments, comprising:
      a flexible first cover connected to the first face of the sheet member, the first cover forming with the sheet member a first pocket compartment having a opening for providing access to the first pocket compartment, a portion of the medical kit members being retained within the first pocket compartment;
      a flexible second cover connected to the first face of the sheet member, the second cover forming with the sheet member a second pocket compartment having an opening for providing access to the second pocket compartment, a portion of the medical kit members being retained within the second pocket compartment, the first pocket compartment disposed near and spaced a distance from the second pocket compartment, the first cover and the second cover cooperating to form an envelope pocket compartment between the first and second pocket compartments, the envelope pocket compartment having an opening thereto disposed between the first and second pocket compartments; and
      closure means having a portion connected to each cover near the respective opening for sealing each compartment;
   closure means connected to the outer peripheral edge of the sheet for selectively maintaining the sheet in the folded position so that the compartment pockets supported on the first face of the sheet are sealed from the outside environment when the sheet is in the folded position, the closure means comprising:
      a zipper assembly connected to the outer peripheral edge of the sheet member, the zipper assembly having an open position and a closed position, the sheet member being positionable in the unfolded position in the open position of the zipper assembly, and the sheet member being maintained in the folded position in the closed position of the zipper assembly so that the pocket compartments supported on the first face of the sheet member are sealed from the effects of the outside environment;
   support means for attaching the sheet member to the back of a person so that the second face of the sheet member is positioned substantially along the person's back, the support means comprising:
   a pack support frame generally shaped to conform to the back of the person, having a plurality of spaced apart post members, each post member having a bore therethrough;
   strap means for attaching the pack support frame to the person so that the frame is positioned against the back of the person; and
   connector means for connecting the flexible sheet member to the pack support frame, the connector means comprising:
      a plurality of ring members equal in number to the number of post members and connected to the second face of the sheet member, each one of the ring members disposable over one of the post members; and
      at least one retainer rod insertable through the bores of the post members and retainable therein to lock the ring members onto the post members so that the sheet member is secured to the pack support frame.

2. The apparatus of claim 1 wherein the sheet member is further characterized as comprising:
   a first end portion generally defining the first end of the sheet, the first end portion being substantially encompassed via portions of the first face, the second face and the outer peripheral edge;

a second end portion generally defining the second end of the sheet, the second end portion being substantially encompassed via portions of the first face, the second face and the outer peripheral edge;

a medial portion substantially connecting the first end portion and the second end portion, the medial portion being substantially encompassed via portions of the first face, the second face and the outer peripheral edge, the medial portion being foldably connected to the first end portion at a first fold-line, and being foldably connected to the second end portion at a second fold-line, the first and second fold-lines extending across a medial portion of the width of the sheet in a generally parallel, spaced-apart relationship;

a right side portion extending generally transversely from the first end portion, the right side portion being substantially encompassed via portions of the first face, the second face, the first end portion and the outer peripheral edge, the right side portion being connected to the first end portion at a third fold-line, the right side portion extending a distance longitudinally with the sheet member from near the first end of the sheet to near the first fold-line; and a left side portion extending generally transversely from the first end portion opposite the right side portion, the left side portion being substantially encompassed via portions of the first face, the second face, the first end portion and the outer peripheral edge, the left side portion being connected to the first end portion at a fourth fold-line, the left side portion extending from near the first end of the sheet to near the first fold-line, the second end portion disposed generally away from the first end portion and the right side portion, and the left side portion extending generally transversely away from the first end portion, in the unfolded position of the sheet member, and the sheet member generally folded in half so that the first face of the second end portion is positioned generally upon the first face of the first end portion via the medial portion and the first and second fold-lines, the right side portion and the left side portion being folded via the third fold-line and the fourth fold-line to substantially encompass respective sides of the second end portion.

* * * * *

UNITED STATES PATENT OFFICE
CERTIFICATE OF CORRECTION

Patent No. 4,169,550    Dated October 2, 1979

Inventor(s) Paul K. Williams

It is certified that error appears in the above-identified patent and that said Letters Patent are hereby corrected as shown below:

In column 7, line 9, "passed" should be --pressed--.

Column 9, line 20, after the word "flap", add the word --top--.

In column 9, line 47, "department" should be --compartment--.

In column 17, line 28, the numeral "2" should be --6--.

*Signed and Sealed this*

*Twenty-second* Day of *January 1980*

[SEAL]

Attest:

SIDNEY A. DIAMOND

*Attesting Officer*

*Commissioner of Patents and Trademarks*